(12) United States Patent
Coyle

(10) Patent No.: US 12,097,350 B2
(45) Date of Patent: Sep. 24, 2024

(54) ROTARY ACTIVATED UNIVERSAL CONNECTOR CAP

(71) Applicant: Becton, Dickinson and Company, Franklin Lakes, NJ (US)

(72) Inventor: Sean Coyle, Pennington, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 543 days.

(21) Appl. No.: 17/297,661

(22) PCT Filed: Nov. 26, 2019

(86) PCT No.: PCT/US2019/063243
§ 371 (c)(1),
(2) Date: May 27, 2021

(87) PCT Pub. No.: WO2020/112767
PCT Pub. Date: Jun. 4, 2020

(65) Prior Publication Data
US 2022/0040469 A1    Feb. 10, 2022

Related U.S. Application Data

(60) Provisional application No. 62/773,539, filed on Nov. 30, 2018.

(51) Int. Cl.
*A61M 39/20*    (2006.01)
*A61M 39/16*    (2006.01)
(Continued)

(52) U.S. Cl.
CPC ............ *A61M 39/20* (2013.01); *A61M 39/16* (2013.01); *F16L 55/1152* (2013.01); *A61M 2039/1038* (2013.01)

(58) Field of Classification Search
CPC .. A61M 39/20; A61M 39/16; A61M 2039/10; F16L 55/1152
(Continued)

(56) References Cited

U.S. PATENT DOCUMENTS 3,326,243 A * 6/1967 Augustus ............ F16L 55/1286
138/90
5,413,561 A * 5/1995 Fischell ................ A61M 39/20
604/167.01

(Continued)

FOREIGN PATENT DOCUMENTS

EP    2121115 B1    11/2015
EP    2595692 B1    12/2020
(Continued)

*Primary Examiner* — David R Deal
(74) *Attorney, Agent, or Firm* — Dickinson Wright PLLC

(57) ABSTRACT

Universal disinfecting connector, connector or cap can interface with male, female, female stopcock, and female hemodialysis threaded fittings, therefore encompassing an entire spectrum of disinfecting connectors. Disinfecting connector or cap includes a configuration of structural elements that provide a universal rotary cap incorporating rotary-activated interfaces and design features allowing the cap to be configured to selectively present any one of a plurality of connection types, or interfaces, for engaging, coupling, or capping, a corresponding type of a male or a female connector or luer.

28 Claims, 14 Drawing Sheets

(51) Int. Cl.
*F16L 55/115* (2006.01)
*A61M 39/10* (2006.01)

(58) Field of Classification Search
USPC .................................... 138/96 R, 96 T, 89
See application file for complete search history.

(56) References Cited

U.S. PATENT DOCUMENTS

| | | | |
|---|---|---|---|
| 6,261,270 B1* | 7/2001 | Gault | A61M 39/20 604/905 |
| 7,166,086 B2* | 1/2007 | Haider | A61M 37/00 604/290 |
| 8,951,057 B2* | 2/2015 | Linder | H01R 13/187 439/314 |
| 10,557,580 B2* | 2/2020 | Mendyk | F16L 37/098 |
| 2006/0030827 A1 | 2/2006 | Raulerson et al. | |
| 2008/0132880 A1 | 6/2008 | Buchman | |
| 2011/0015580 A1* | 1/2011 | Stroup | A61M 39/12 604/207 |
| 2012/0312411 A1* | 12/2012 | Lubbers | B65D 59/06 138/96 R |
| 2012/0319401 A1* | 12/2012 | Wang | F16L 37/0985 285/363 |
| 2014/0228773 A1 | 8/2014 | Burkholz | |
| 2017/0056639 A1 | 3/2017 | Ma | |
| 2018/0256880 A1 | 9/2018 | Follman | |

FOREIGN PATENT DOCUMENTS

| | | |
|---|---|---|
| JP | 2008506465 A | 3/2008 |
| JP | 2016511111 | 4/2016 |
| JP | 2016512117 A | 4/2016 |
| WO | WO-2011066565 A1 | 6/2011 |
| WO | WO-2016147555 A1 | 9/2016 |

* cited by examiner

ROTARY ACTIVATED UNIVERSAL CONNECTOR CAP

CROSS-REFERENCE TO RELATED APPLICATIONS

This application claim priority under 35 USC § 119(e) from U.S. Provisional Patent Application No. 62/773,539 filed on Nov. 30, 2018, the contents of which (including all attachments filed therewith) are hereby incorporated by reference in their entirety.

TECHNICAL FIELD

Generally, exemplary embodiments of the present disclosure relate to the fields of threaded fittings, including medical caps and medical disinfection caps, and in particular caps and/or disinfection caps for uses with male, female, female stopcock, and female hemodialysis threaded fittings.

BACKGROUND

In the example of medical applications, various conventional caps for closing off a needleless connector while not in use have been known for some time. In order to decrease Catheter-related bloodstream infection (CRBSI) cases disinfection caps were originally disclosed in U.S. Patent Publication No. 2007/011233 which issued as U.S. Pat. No. 8,740,864 (the entire disclosures of both of which are incorporated herein by reference), and introduced on the market. Disinfection caps such as those disclosed in the U.S. Pat. No. 8,740,864 are illustrated in FIGS. 1A and 1B herein, where cap 1 includes a disinfecting pad 2 and a lid 3, and cap 4 includes a disinfecting pad 5 and lid 7, as well as threads 6 on its inner circumference 8 to interlock with needleless connector hub. On the other hand, other conventional caps may have similar features but exclude the disinfecting pad. Further improved designs for disinfection caps are disclosed in related U.S. patent application Ser. Nos. 15/408,278 and 15/408,187, both filed on Jan. 17, 2017 (the entire disclosures of both of which are incorporated herein by reference). Yet further modifications to cap designs adding further safety considerations are disclosed in related U.S. Patent Application Nos. 62/488,266, filed on Apr. 21, 2017, 62/523, 506, filed Jun. 22, 2017, and 62/623,858 filed Jan. 30, 2018 (the entire disclosures of which are incorporated herein by reference).

Currently, there are male disinfecting cap devices for disinfecting ISO594-2 type of female threaded fluid luer connectors and there are female disinfecting cap devices for disinfecting ISO594-2 type of male threaded fluid luer connectors. While there are dual purpose caps that may be capable of capping a certain male and/or female threaded luer connector, such caps are not capable of capping an entire spectrum of connectors in a single cap.

Current cap spectrum encompasses the following types: cap or disinfecting cap devices for disinfecting ISO594-2 type of male threaded connectors; cap or disinfecting cap devices for disinfecting ISO594-2 type of female threaded connectors; cap or disinfecting cap devices for disinfecting ISO594-2 type of female threaded hemodialysis connectors; and cap or disinfecting cap devices for disinfecting ISO594-2 type of open-female connection threaded connectors on stopcocks, designed to maintain pressure in the stopcock.

However, there is not a singular universal cap, or disinfecting cap, designed to interface with male, female, female stopcock, and female hemodialysis threaded fittings, therefore encompassing the entire spectrum of connectors including all four male or female types of ISO594-2 connectors.

SUMMARY

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

As would be readily appreciated by skilled artisans in the relevant art, while descriptive terms such as "lock", "hole", "tip", "hub", "thread", "sponge", "protrusion", "tab", "slope", "wall", "top", "side", "bottom," "lower," "upper," "fitting," "stopcock" and others are used throughout this specification to facilitate understanding, it is not intended to limit any components that can be used in combinations or individually to implement various aspects of the embodiments of the present disclosure.

Exemplary embodiments of the present disclosure provide a structure for a single universal disinfecting connector, connector or cap which can interface with male, female, female stopcock, and female hemodialysis threaded fittings, therefore encompassing an entire spectrum of disinfecting connectors. For example, from a clinical perspective, a disinfecting connector or cap according to the present disclosure advantageously reduces the number of device types and logistics that is currently needed in the hospital setting from 4 to 1.

In an exemplary implementation of the embodiments of present disclosure, a connector, a cap, a connector cap, or a disinfecting cap may have applications for use in medical applications such as fittings, for example pertaining to ISO594-2 fluid luer connectors, as well as general non-medical related threaded fittings applications.

According to exemplary embodiments of the present disclosure, configuration of structural elements provide a universal rotary cap that incorporates a rotary-activated interfaces and design features allowing the cap to be configured to selectively present any one of a plurality of connection types, or interfaces, for engaging, coupling, or capping, a corresponding type of a male or a female connector or luer.

According to exemplary implementations of the embodiments of the present disclosure, a connector or cap structure comprises a combination of features including a rotary base, or a bottom casing, a housing, or top casing, axially fixed with respect to the rotary base and having an open end designed to interface or connect with female threaded connectors, female threaded hemodialysis connectors, and/or female open connection threaded connectors, and a slide disposed within the housing with respect to the rotary base and designed to facilitate connection or interface of the cap with female and/or male threaded connectors.

According to exemplary implementations of the embodiments of the present disclosure, rotary base of the connector or cap can be configure to be rotatable with respect to the housing to activate the cap design features that facilitate male or female-type connection of the cap, for example by allowing the slide to move axially with respect to the housing. In an exemplary implementation, the rotary base includes a protrusion, for example a threaded protrusion, designed to interface with the slide to facilitate or cause movement of the slide with respect to the housing, for example to ride up and down the protrusion, due to a relative rotation of the rotary base with respect to the housing. In an exemplary implementation, the slide is rotationally fixed with respect to the housing, but can move axially with respect to the housing.

According to another exemplary implementations of the embodiments of the present disclosure, a connector or cap comprises an additional design feature, such as a rod, or a pressure rod, to facilitate an open-female type connection.

According to still further exemplary implementations of the embodiments of the present disclosure, the open end of the housing can be configured with an inner protrusion, or thread, designed to engage an outer protrusion, or a thread, of a female connector.

In yet further exemplary implementation, the slide can selectively extend out of the housing to facilitate connection or interface of the cap with male threaded connectors. For example, and end portion of the slide extending out of the housing can be configured with an outer protrusion, or thread, designed to engage a protrusion, or a thread, of a male connector such as a protrusion or thread disposed in a collar of the male connector.

According to still further exemplary implementations of the embodiments of the present disclosure, a connector or cap structure includes features designed to disinfect a male of female connection for example by providing a cleaning solution at an open end of the housing of the cap structure.

According to still further exemplary implementations of the embodiments of the present disclosure, an open end of a connector or cap structure can be provided with a peel sealing film to maintain sterility of the connection interfaces and/or preserve a cleaning solution if included.

Any combination of such exemplary implementations can be provided in the connector or cap structure of the present disclosure

BRIEF DESCRIPTION OF THE DRAWINGS

Referring now to the drawings, wherein like reference numerals designate identical or corresponding parts throughout the several views, embodiments of the present disclosure are described as follows.

DETAILED DESCRIPTION OF THE EXEMPLARY EMBODIMENTS

This matters exemplified in this description are provided to assist with a comprehensive understanding of exemplary embodiments with reference to the accompanying drawing figures. Accordingly, those of ordinary skill in the art will recognize that various changes and modifications of the exemplary embodiments described herein can be made within the scope of appended claims without departing from their full scope and equivalents. Also, descriptions of well-known functions and constructions are omitted for clarity and conciseness. Likewise, certain naming conventions, labels and terms as used in the context of the present disclosure are non-limiting and provided only for illustrative purposes to facilitate understanding of exemplary implementations of the exemplary embodiments.

Referring to FIGS. 2 through 6D, according to exemplary embodiments of the present disclosure a cap structure 10 comprises, a housing 20, a base 30, and a slide 40

Figure 10A:
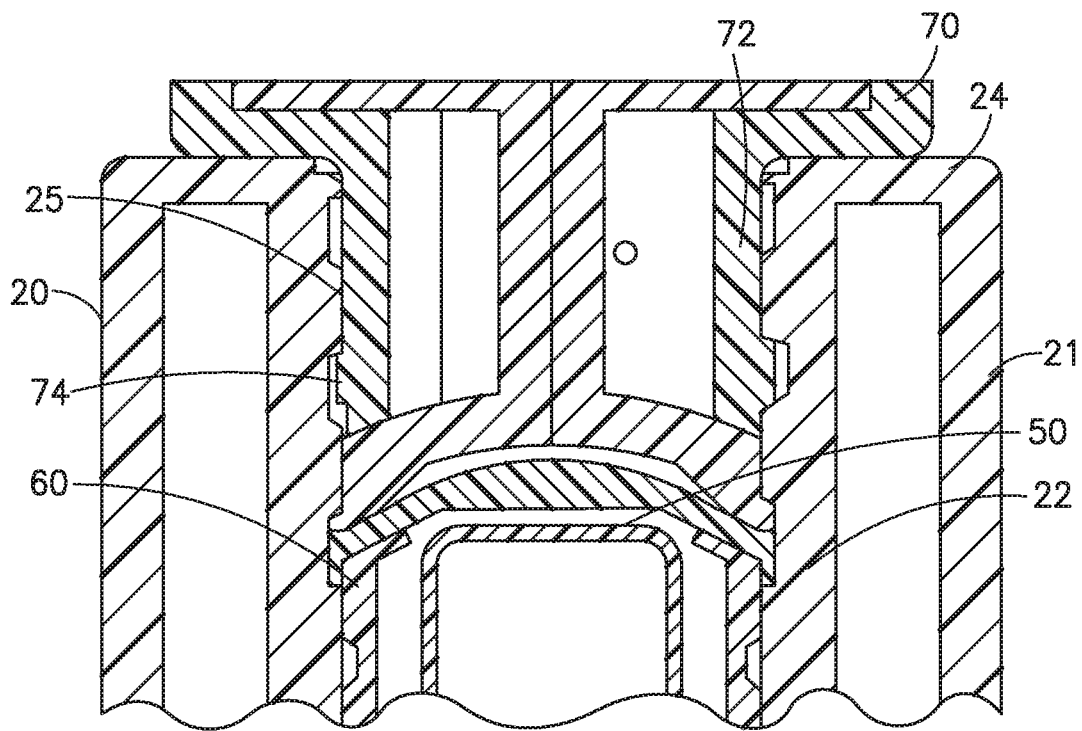
FIG. 10A diagrammatically shows a cross sectional view of a cap structure, such as those of FIGS. 2 and 7, capping a female connector or luer.

According to an exemplary implementation, housing 20 can be configured to include an essentially cylindrical exterior sidewall 21 defining opening 26 at bottom of housing 20 into a major cavity 29 configured to accommodate slide 40 therein, and an essentially cylindrical interior sidewall 22 forming an opening 23 at top of housing 20 into a cavity 27 configured to receive, or interface with, female threaded connectors, female threaded hemodialysis connectors, and/or female open connection threaded connectors, as diagrammatically illustrated in FIG. 10A showing a connector 70. A shoulder, lip, or top wall 24 can connect exterior sidewall 21 and interior sidewall 22. In an exemplary implementation, housing 20 can be a unitary structure formed by exterior sidewall 21, top wall 24, and interior sidewall 22. In yet another exemplary implementation, interior surface of the interior sidewall 22 includes a protrusion, a thread, or a partial thread 25 configured to engage a corresponding structure, such as a thread or protrusion 74, on an external surface of a female connector 70 received into cavity 27 (see FIG. 10A).

According to an exemplary implementation, base, or rotary base, 30 includes a sidewall 35 and a bottom wall 34, where, in an exemplary implementation, bottom wall 34 forms bottom of cap 10. According to further exemplary implementation, a protrusion 31 extends from interior surface of bottom wall 34 essentially perpendicular to the bottom wall 34. In an exemplary implementation, protrusion 31 is a cantilevered protrusion and can include a thread 32. Base 30 and housing 20 are rotationally engaged, for example by engagement of exterior sidewall 21 of housing 20 and sidewall 35 of base 30, for example by means of a snap fit connection via complimentary protrusion 36 on exterior surface of sidewall 35 of base 30 and groove 28 on interior surface of exterior sidewall 21 of housing 20, such that base 30 and housing 20 are essentially axially fixed with respect to each other and essentially free to rotate with respect to each other.

According to an exemplary implementation, slide, or slide connector interface, 40 comprises an essentially cylindrical structure that includes an essentially cylindrical first, or upper, portion 41 and an essentially cylindrical second, or lower, portion 42. An essentially cylindrical cavity 46 extends coaxially and through the first portion 41 and the second portion 42. An interior surface of the second portion 42 forms a lower portion of cavity 46, and in an exemplary implementation interior surface of the second portion 42 includes one or more protrusions or threads 47 that cooperate(s) with the thread 32 of protrusion 31 of base 30 allowing slide 40 to move axially with respect to protrusion 31 due to rotation of slide 40 with respect to protrusion 31, for example such that slide 40 rides along the protrusion 31 of base 30 to achieve linear actuation of slide 40.

Exterior circumference of first portion 41 is such that first portion 41 can slide through cavity 27 and extend out of opening 23 of housing 20. Interior surface of first portion 41 forms an upper portions of cavity 46 capable of receiving or accommodating a tip or hub 82 of a male connector 80 (see FIG. 10B). An exterior surface of first portion 41 can include a protrusion, a thread, or a partial thread 45 configured to engage a corresponding structure, such as an inner thread or protrusion 86 on collar 84, of connector 80.

In a further exemplary implementation, slide 40 includes one or more guide rails 44 along exterior surface of slide 40, for example exterior of the second portion 42, which interface(s) with the interior, for example one or more rails or protrusion 290, of the housing 20 to facilitate the linear actuation of slide 40, as well as keep the slide, or slide connector interface, 40 stable when interfacing with a male luer tip, such as tip or hub 82 of a male connector 80.

Figure 1A:
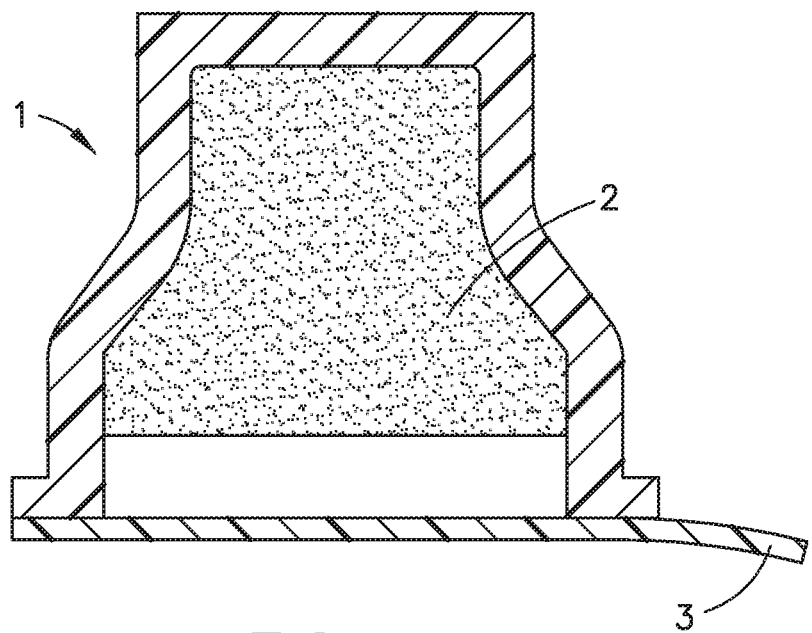
FIGS. 1A and 1B are cross sectional views of conventional caps for needleless connectors.
Figure 1B:
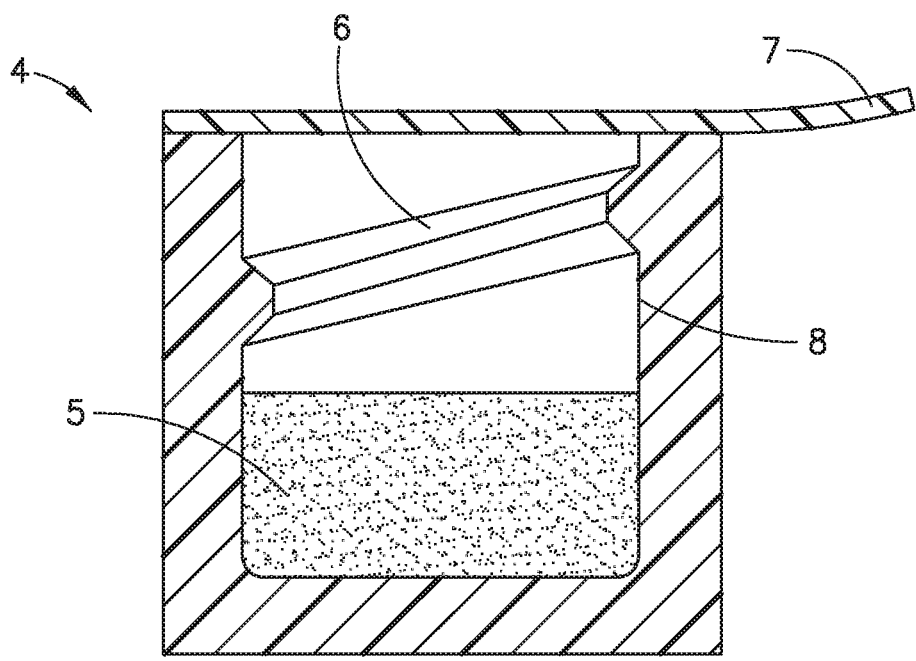
Figure 3:
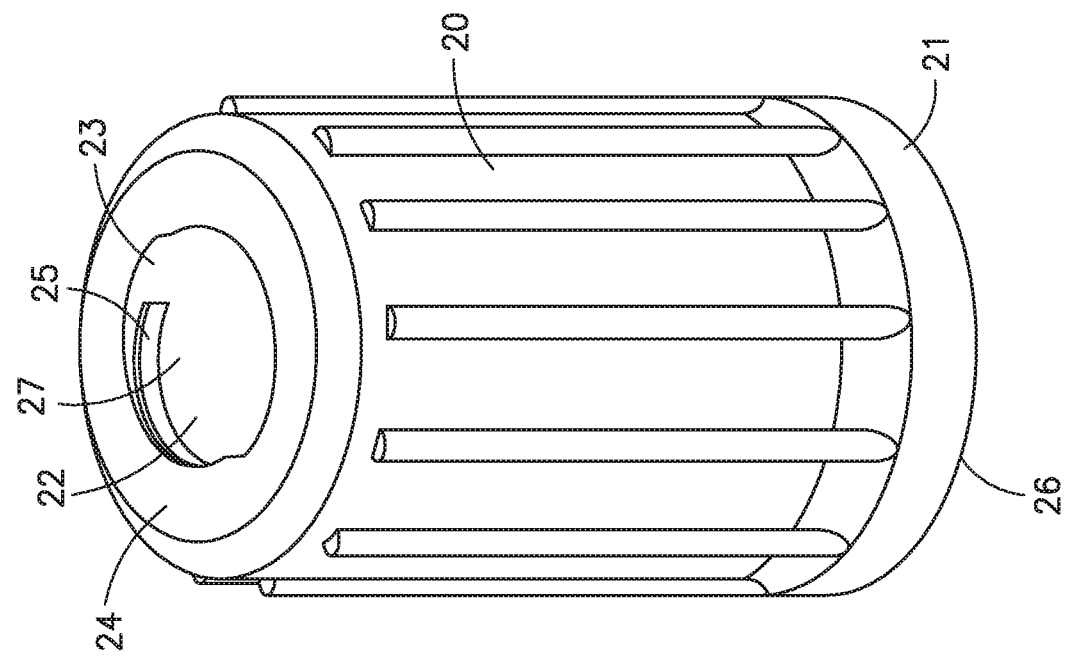
FIG. 3 illustrates an isometric or perspective view of a housing component of a cap structure according to exemplary embodiments of the disclosure.
Figure 2:
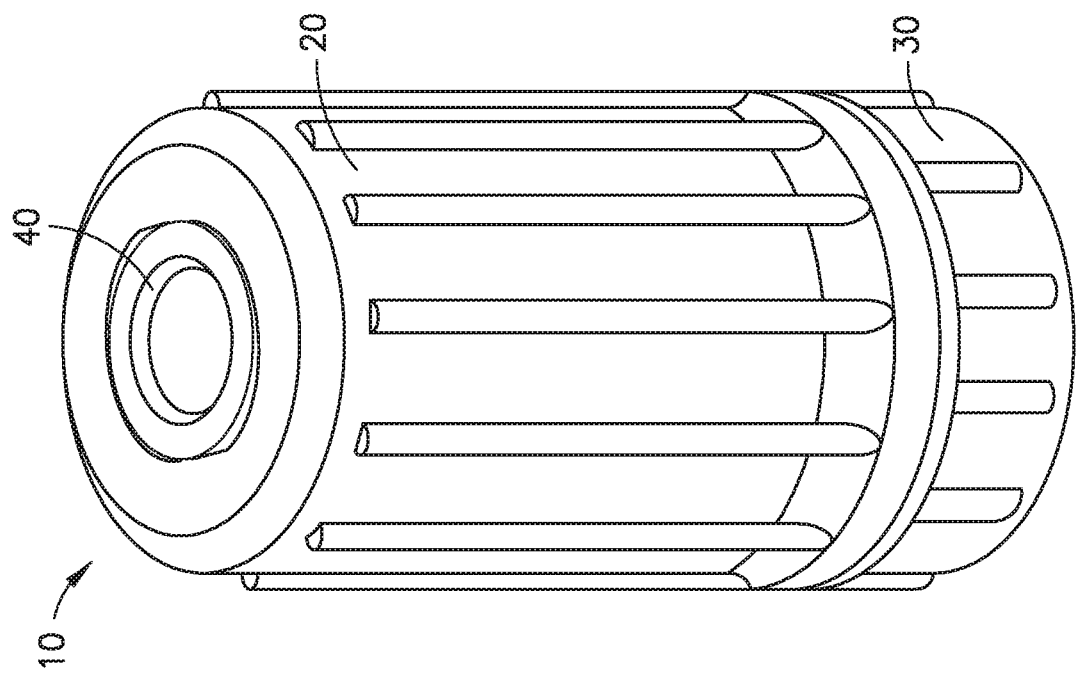
FIG. 2 illustrates an isometric or perspective view of a cap structure according to exemplary embodiments of the disclosure.
Figure 5:
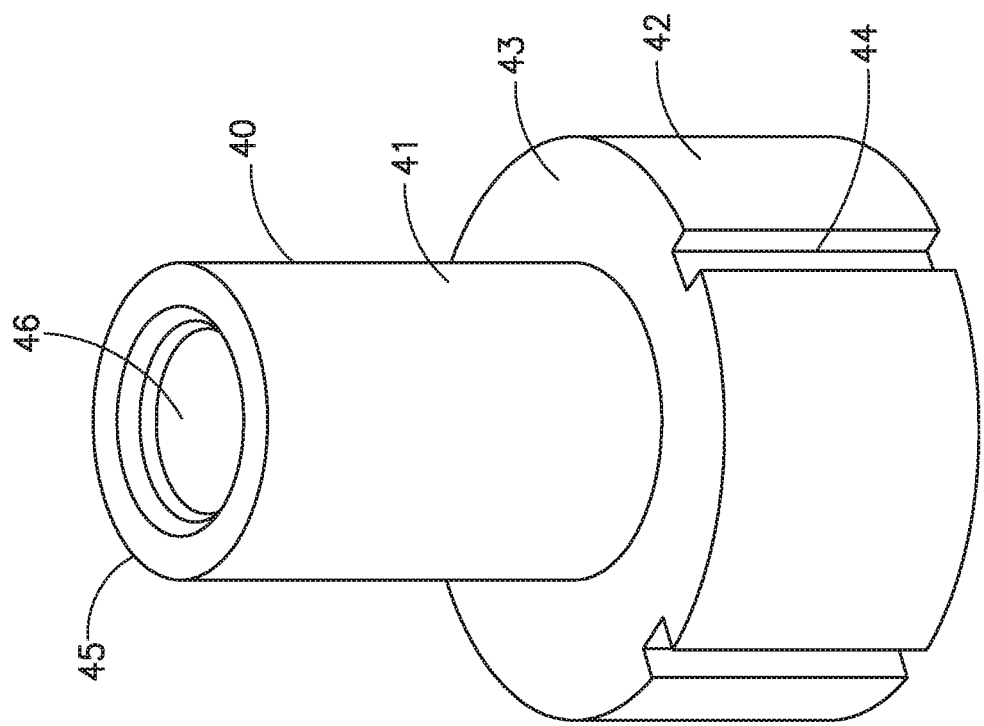
FIG. 5 illustrates an isometric or perspective view of a slide component of a cap structure according to exemplary embodiments of the disclosure.
Figure 4:
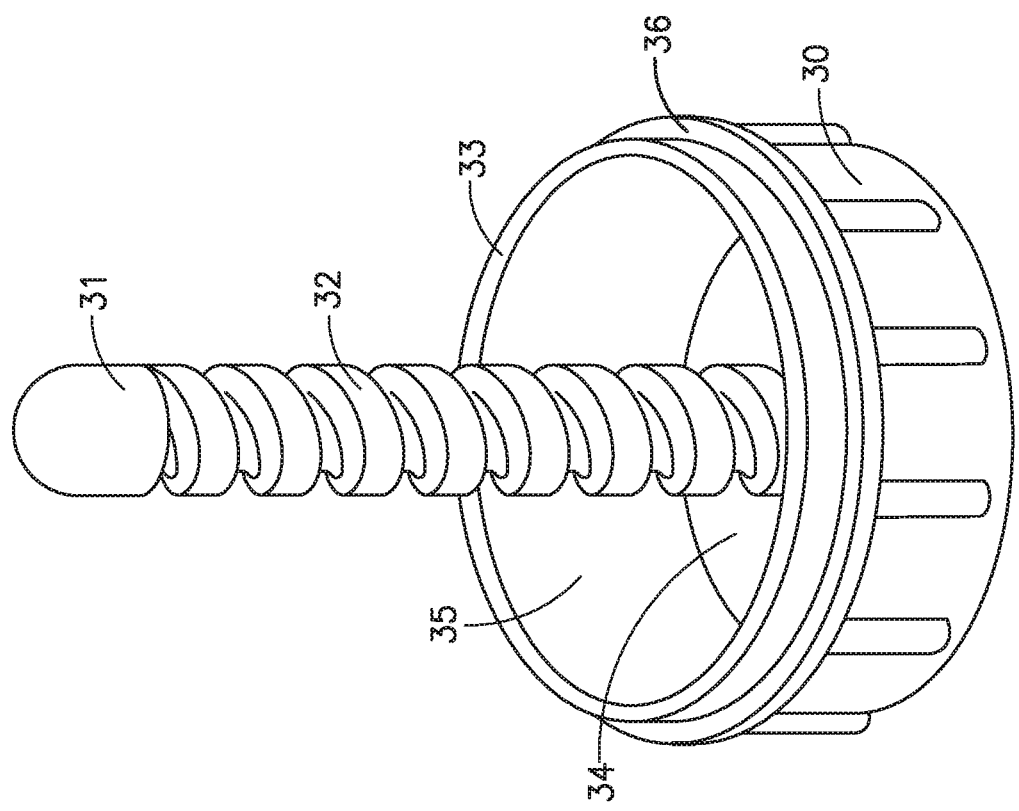
FIG. 4 illustrates an isometric or perspective view of a base component of a cap structure according to exemplary embodiments of the disclosure.
Figure 6A:
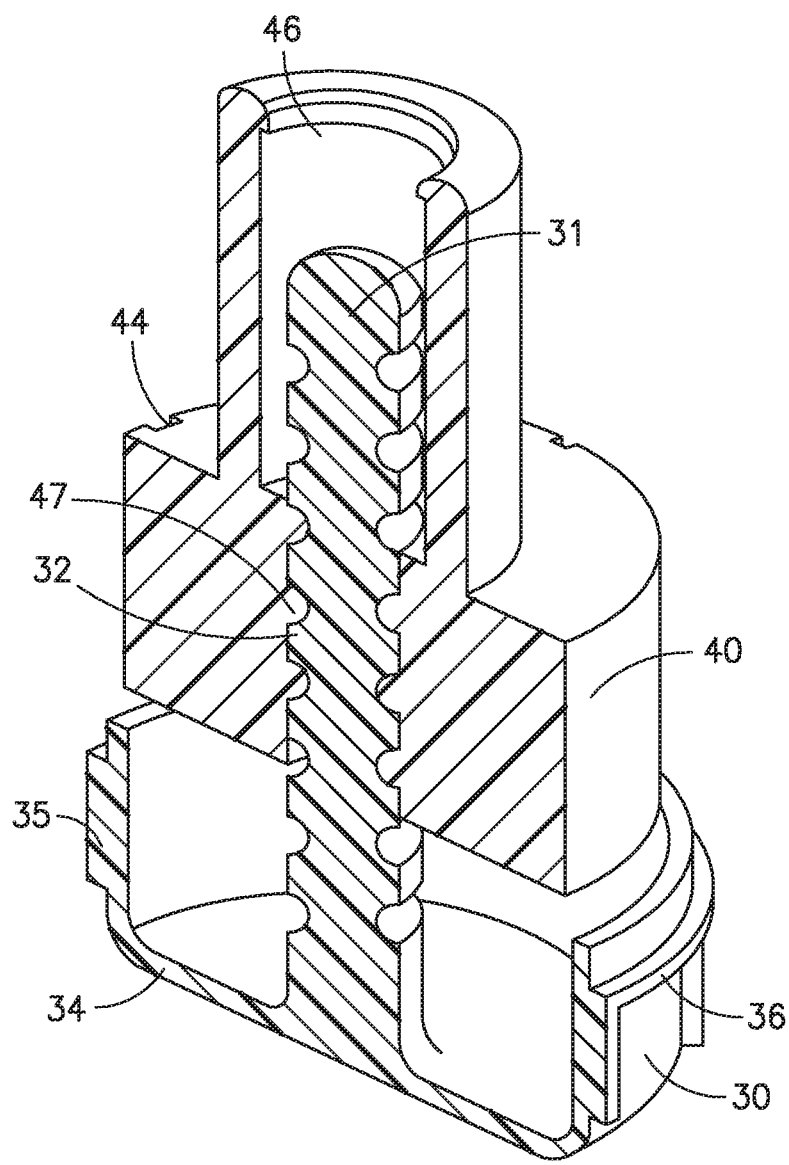
FIG. 6A illustrates an isometric split, or cross sectional, view of a base component with a slide component of cap according to exemplary embodiments of the disclosure.
Figure 6B:
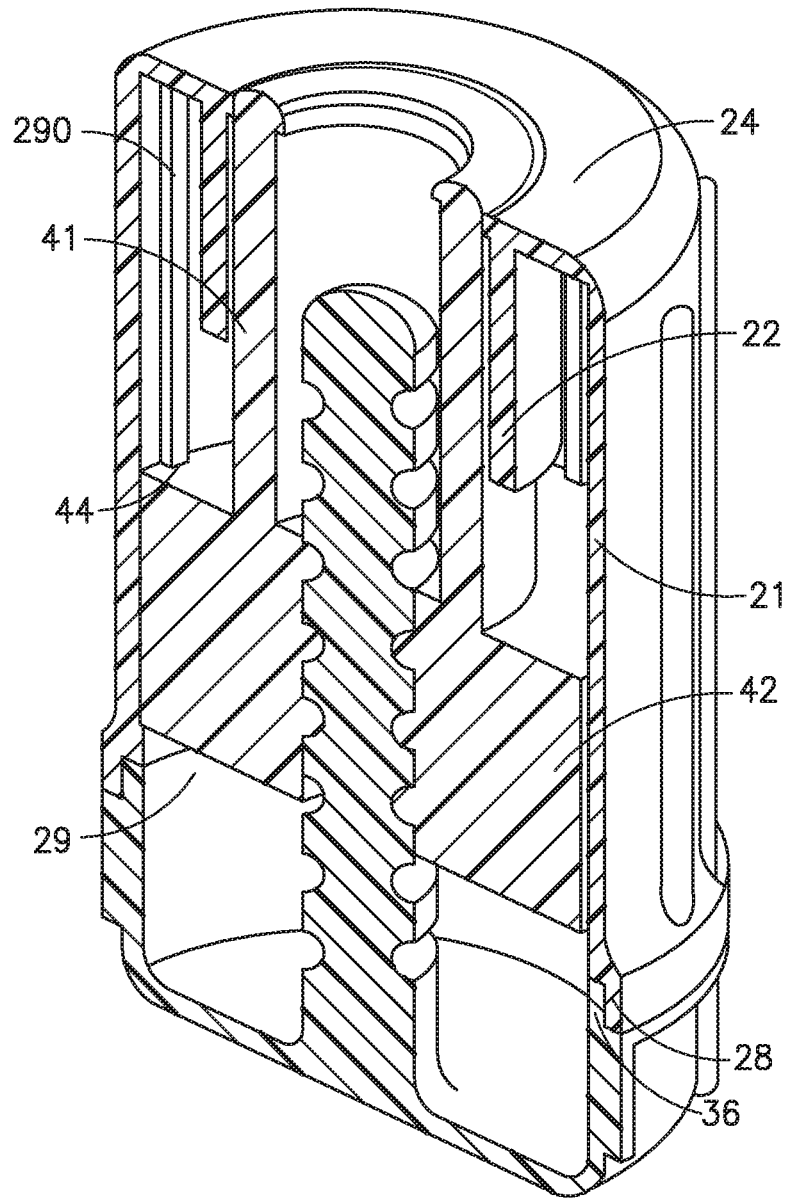
FIGS. 6B, 6C, and 6D diagrammatically show isometric split, or cross sectional, views of a cap at various stages of activation of cap design features or connections, according to exemplary embodiments of the disclosure.
Figure 6C:
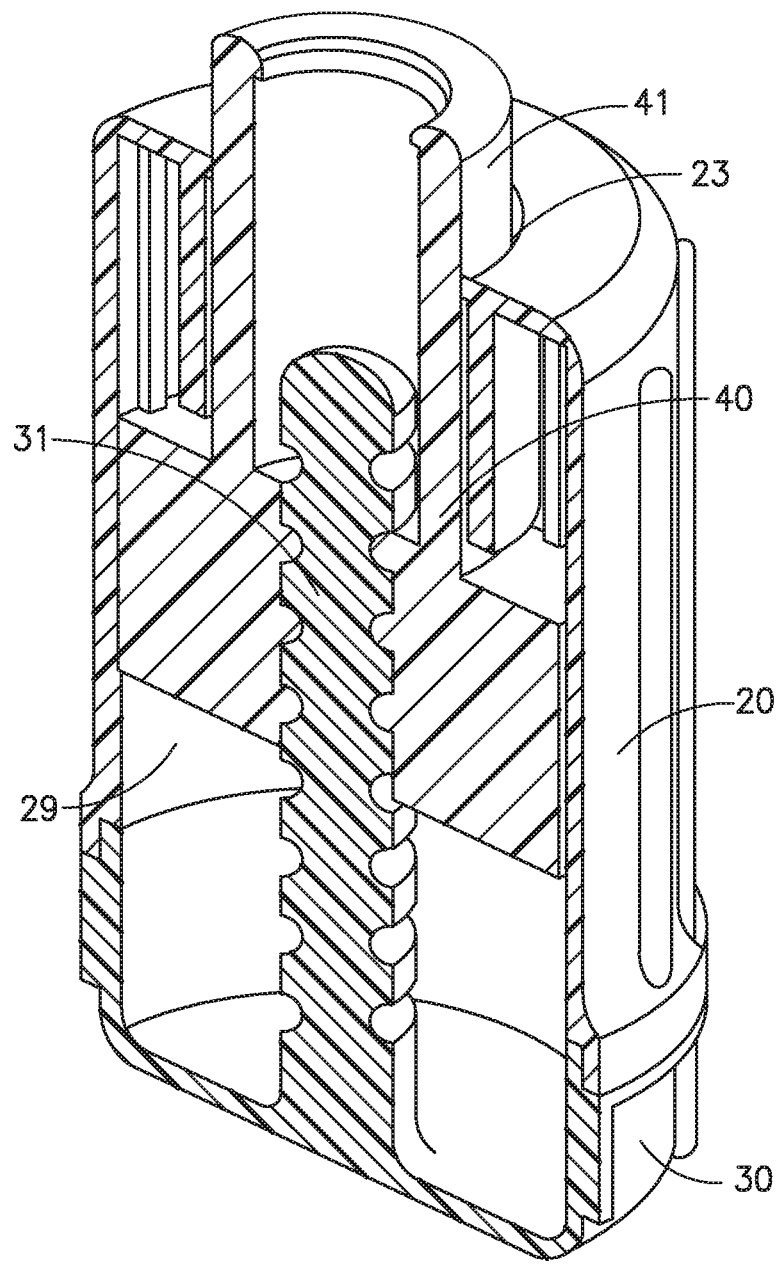
Figure 6D:
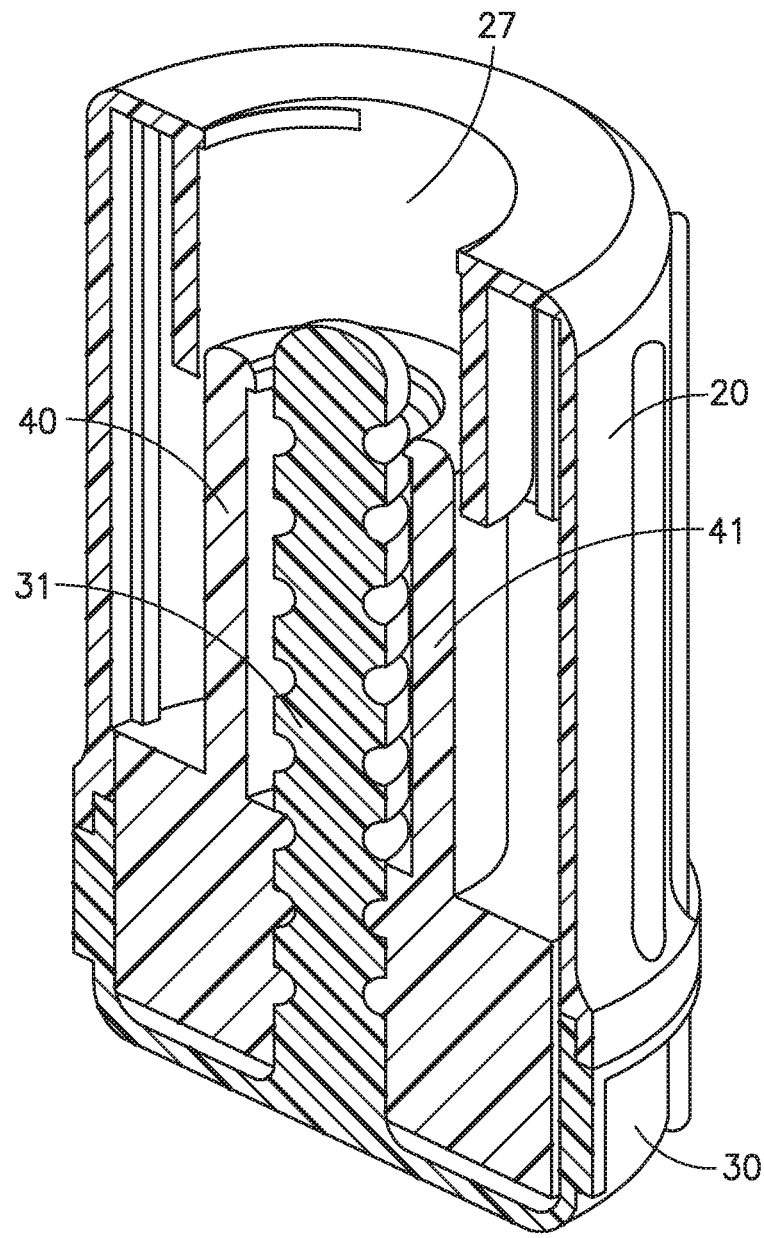
Figure 8A:
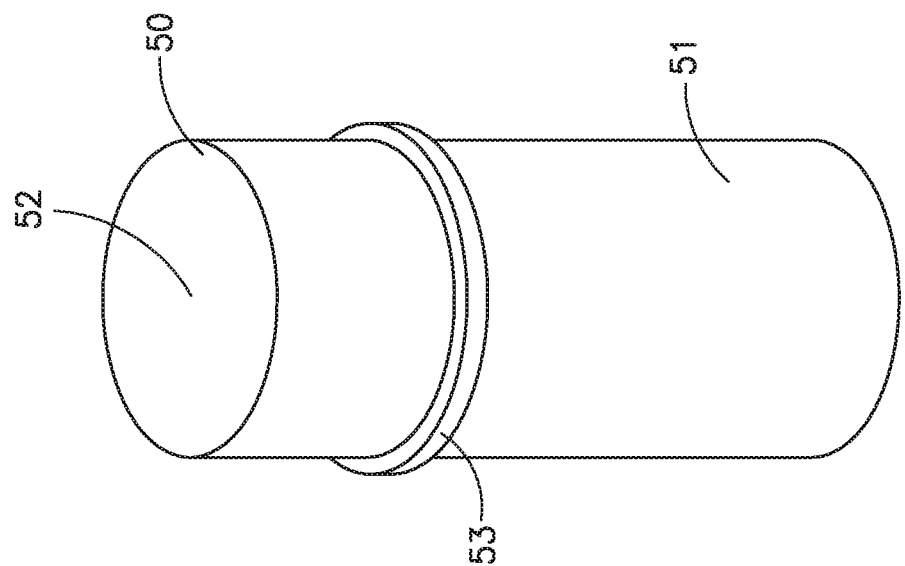
FIG. 8A illustrates an isometric or perspective view of a rod components of a cap structure according to exemplary embodiments of the disclosure.
Figure 7:
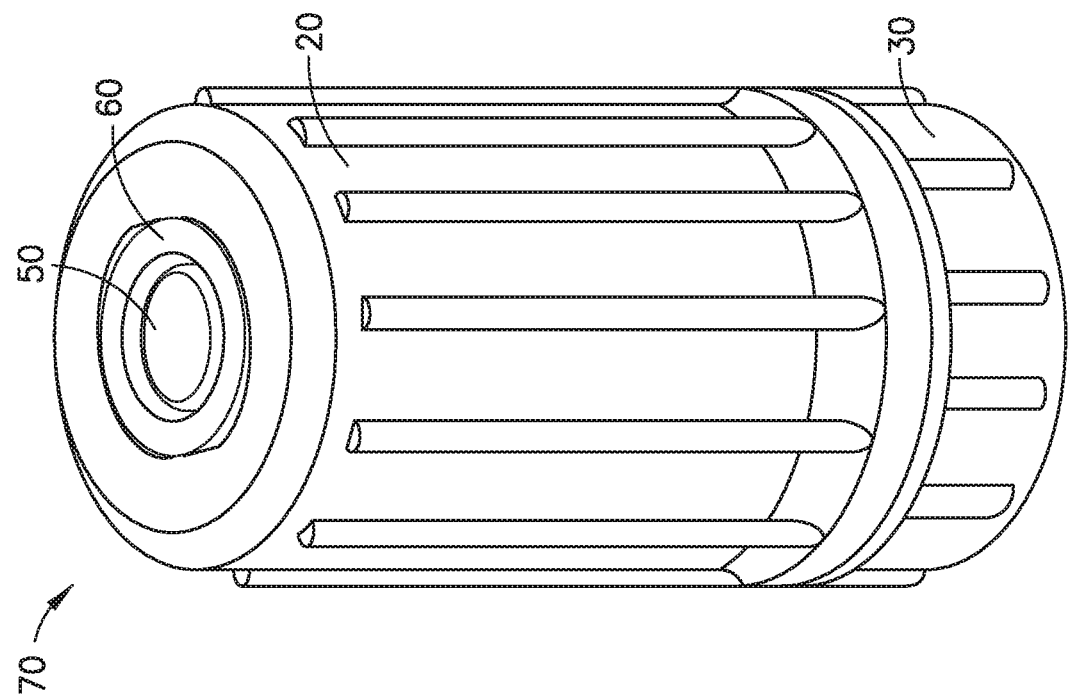
FIG. 7 illustrates an isometric or perspective view of a cap structure according to other exemplary embodiments of the disclosure.
Figure 8B:
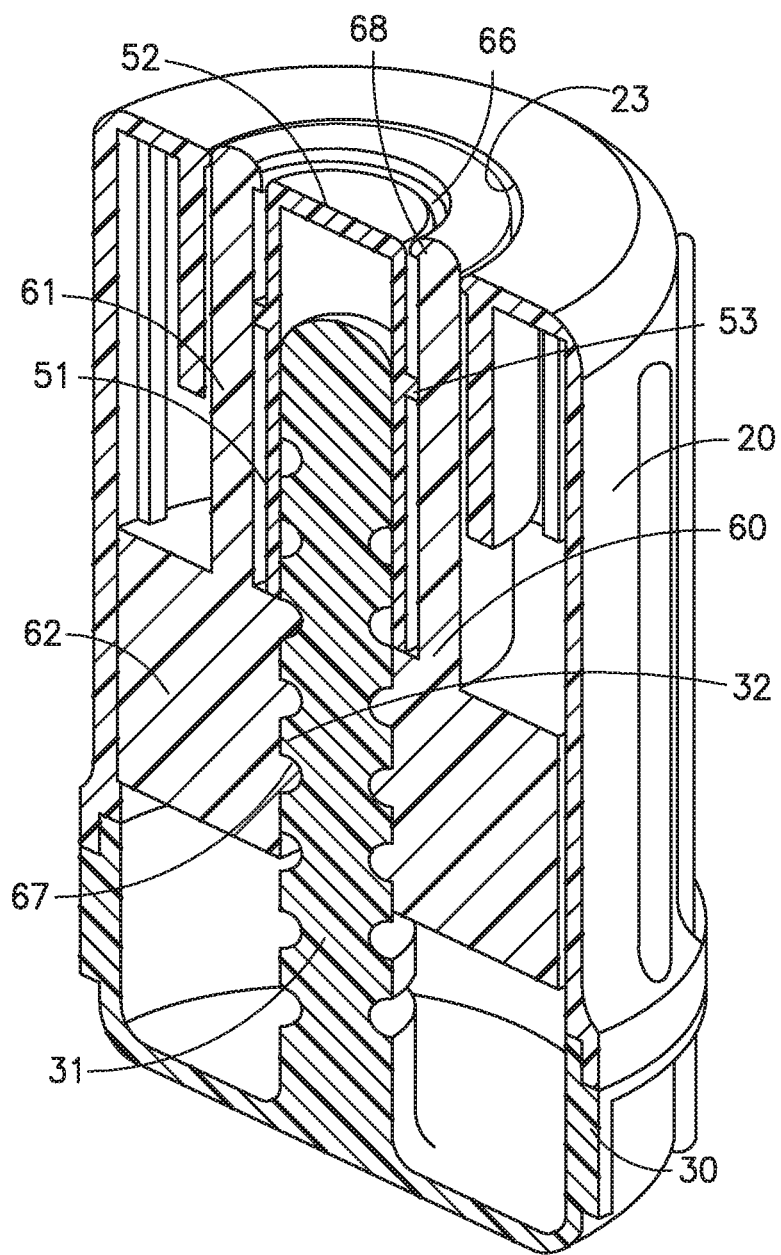
FIG. 8B illustrates an isometric split, or cross sectional, view of a cap structure according to exemplary embodiments of the disclosure.

An example of operation of cap 10 according to exemplary embodiments of the disclosure is described with reference to FIGS. 6B, 6C and 6D, where base or bottom casing 30 can twist or rotate with respect to housing 20 to activate each connection. For example, twisting the base 30 to the right with respect to housing 20 activates male tip connection by axially moving first portion 41 of slide 40 out of top of housing 20 via opening 23 of and locking slide 40 into place as illustrated in the example of FIG. 6C. On the other hand, twisting the base 30 to the left with respect to housing 20 activates female connection by axially moving slide 40 further into housing 20 to open female port formed by cavity 27 by moving first portion 41 of slide 40 out of cavity 27, as illustrated in the example of FIG. 6D.

Referring to FIGS. 7 through 9C, according to exemplary embodiments of the present disclosure a cap structure 70 comprises, a housing 20, a base 30, a slide 60, and a rod 50. According to an exemplary implementation, housing 20 and base 30 of cap 70 can have the same configuration as that of cap 10 described above with reference to examples of FIGS. 2 through 6D.

An additional feature of an exemplary implementation of embodiment of cap 70 incudes a rod, or pressure rod, 50 configured with respect to slide 60.

The pressure rod 50 can sit in the assembly, for example within cavity 66 of slide 60, when the open-female connection is activated in order to maintain pressure, for example in a stopcock. When a general female connection is required, additional twisting of the rotary base 30 can allow the male slide 60 to connect with the pressure rod 50 to pull the pressure rod 50 further into the assembly, thus creating the necessary space within cavity 27 of housing 20 for the general female or hemodialysis female connection.

In an exemplary implementation, rod 50 includes an essentially cylindrical sidewall 51, top wall 52 and cavity 54. Cavity 54 is essentially cylindrical and formed by interior surface of sidewall 51 and interior surface of top wall 52. Cavity 54 is of sufficient diameter and depth to coaxially accommodate therein at least a portion of protrusion 31 of base 30.

According to an exemplary implementation, slide, or slide connector interface, 60 comprises an essentially cylindrical structure that includes an essentially cylindrical first, or upper, portion 61 and an essentially cylindrical second, or lower, portion 62. An essentially cylindrical cavity 66 extends coaxially and through the first portion 61 and the second portion 62. An interior surface of second portion 62 forms a lower portion of cavity 66, and in an exemplary implementation interior surface of second portion 62 includes one or more protrusions or threads 67 that cooperate(s) with the thread 32 of protrusion 31 of base 30 allowing slide 60 to move axially with respect to protrusion 31 due to rotation of slide 60 with respect to protrusion 31, for example such that slide 60 rides long the protrusion 31 of base 30 to achieve linear actuation of slide 60

Figure 10B:
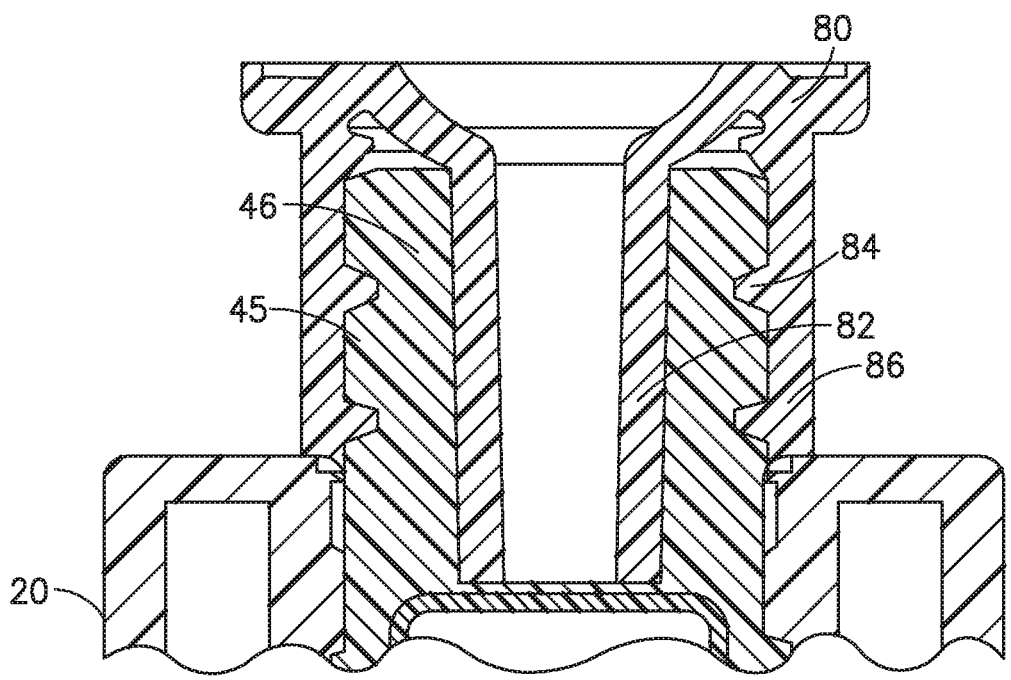
FIG. 10B diagrammatically shows a cross sectional view of a cap structure, such as those of FIGS. 2 and 7, capping a male connector or luer.

In an exemplary implementation, exterior circumference of first portion 61 is such that first portion 61 can slide through cavity 27 and extend out of opening 23 of housing 20. Interior surface of first portion 61 forms an upper portions of cavity 66 capable of receiving or accommodating a tip or hub 82 of a male connector 80 (see FIG. 10B). In addition, interior circumference of first portion 61 forms cavity 66 capable of accommodating therein rod 50, such that sidewall 51 of rod 50 can move axially with respect to interior surface of first portion 61. An exterior surface of first portion 61 can include a protrusion, a thread, or a partial thread 65 configured to engage a corresponding structure, such as an inner thread or protrusion 86 on collar 84, of connector 80 (FIG. 10B).

In an exemplary implementation, exterior surface of sidewall 51 includes a protrusion 53 and interior surface of first portion 61 includes a corresponding protrusion 68. For example, protrusion 68 can be configured near the opening into first portion 61 at the upper portions of cavity 66 and protrusion 53 can be configured at a distance with respect to top wall 52 such that when slide 60 slides axially to open cavity 66 for female connection of cap 70, protrusion 53 abuts protrusion 68 to cause rod 50 to slide with slide 60 to fully open cavity 66.

Figure 9A:
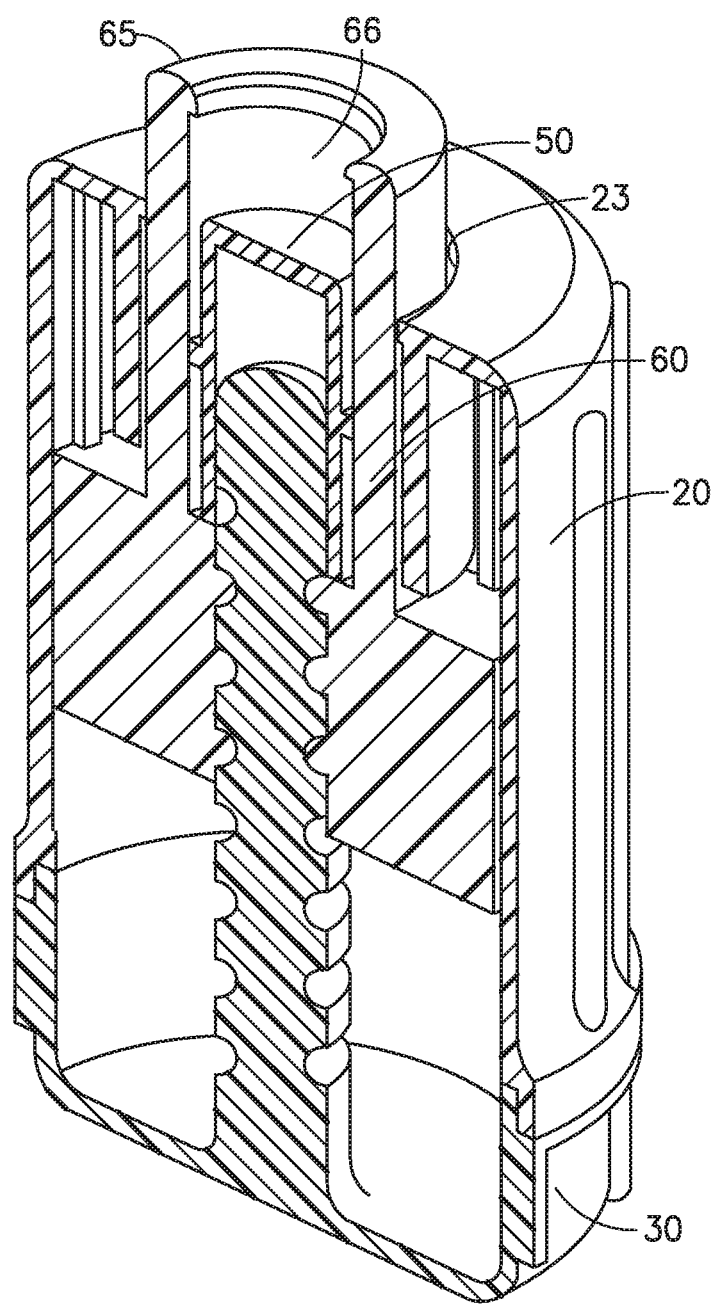
FIGS. 9A, 9B and 9C diagrammatically show isometric split, or cross sectional, views of a cap at various stages of activation of cap design features or connections, according to exemplary embodiments of the disclosure.

An example of operation of cap 70 according to exemplary embodiments of the disclosure is described with reference to FIGS. 9A, 9B, and 9C, where base or bottom casing 30 can twists or rotate with respect to housing 20 to activate each connection. For example, twisting the base 30 to the right with respect to housing 20 activates male tip connection by axially moving first portion 61 of slide 60 out of top of housing 20 via opening 23 and locking slide 60 into place as illustrated in the example of FIG. 9A. Rod 50 can be configured within cavity 66 such that top wall 52 does not prevent upper portions of cavity 66 from receiving or accommodating a tip or hub 82 of a male connector 80 (see FIG. 10B).

Figure 9B:
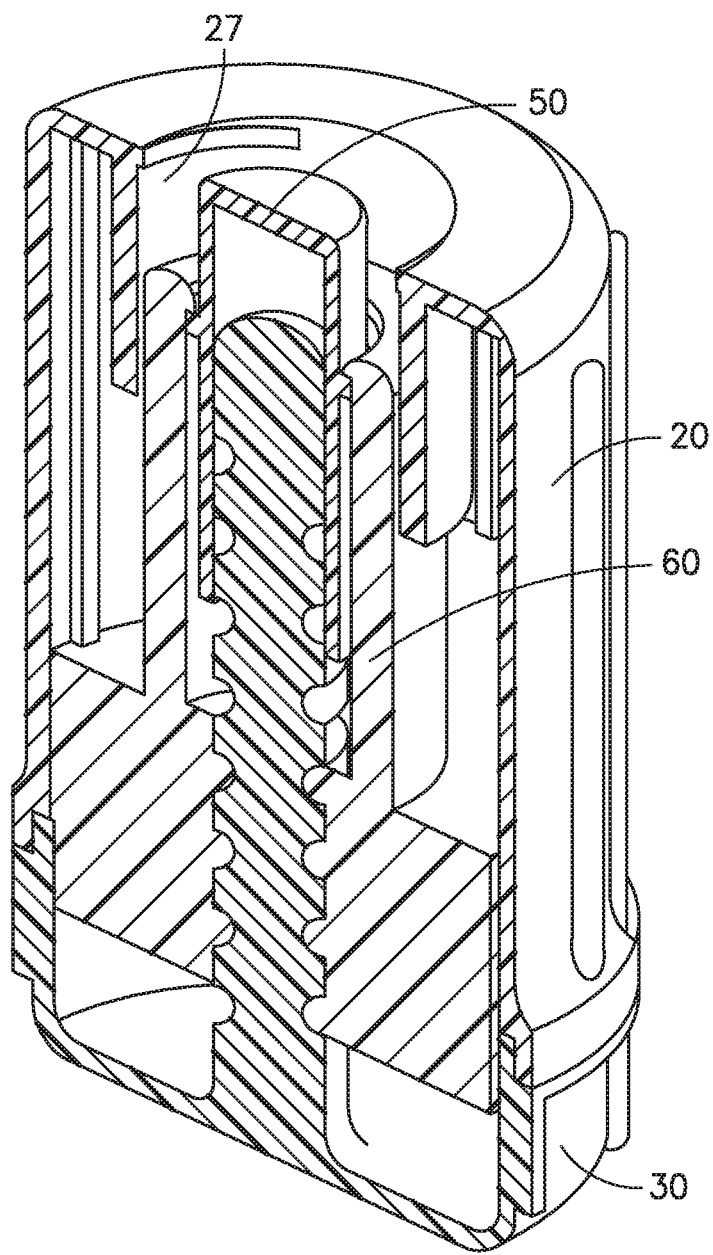
Figure 9C:
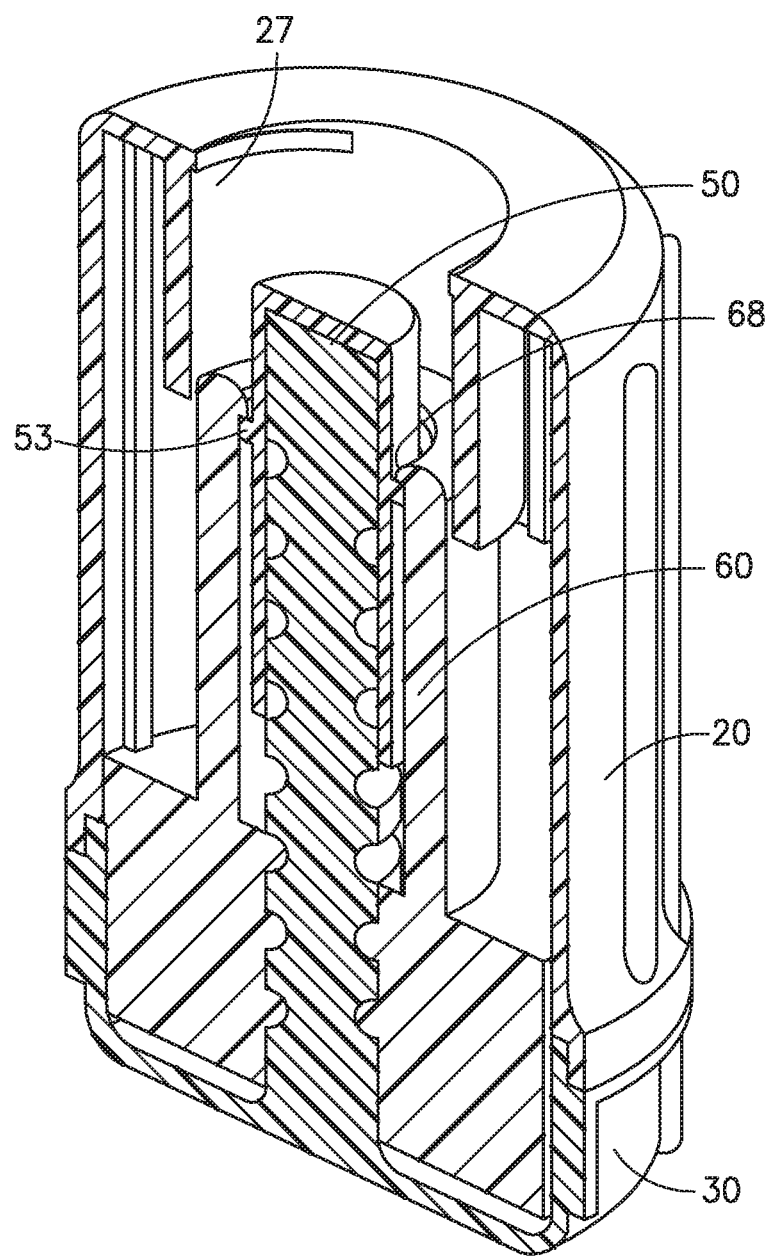

On the other hand, twisting the base 30 to the left with respect to housing 20 activates female connection by axially moving slide 60 further into housing 20 to open female port formed by cavity 27 by moving first portion 61 of slide 60 out of cavity 27 while maintaining rod 50 within cavity 27 to provide IV pressure maintenance for open female connections as illustrated in the example of FIG. 9B (see also a diagrammatic example illustrated in FIG. 10A).

According to a further exemplary implementation, twisting base 30 further to the left with respect to housing 20, for example by 50 degrees, activates a general female connection by causing slide 60 to axially slide down or further into housing 20 and out of cavity 27 to further open cavity 27. During this further operation, rod 50 connects with slide 60 by beans of abutting protrusions 53 and 58 to open female connection port, cavity 27, fully, as illustrated in FIG. 9C.

Figure 11:
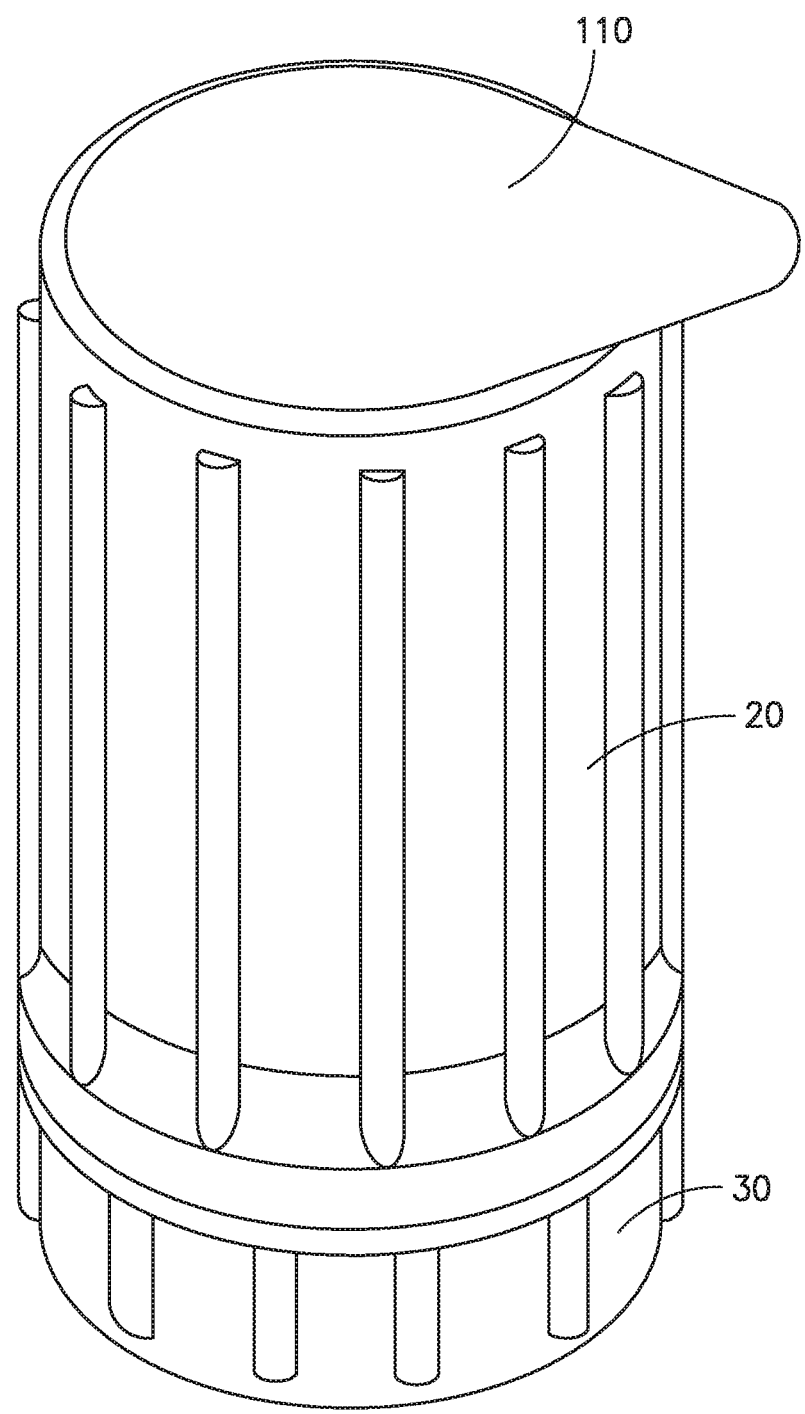
FIG. 11 illustrates an isometric or perspective view of a cap structure, such as those of FIGS. 2 and 7, including a cover, such as a peel strip, according to exemplary embodiments of the disclosure.

Referring to FIG. 11, according to exemplary embodiments of the disclosure, cap 10 or cap 70 can be configured with a peel sealing film 110 sealing cavity 27, for example by attachment to exterior surface of top wall 24 of housing 20. In an exemplary implementation, peel sealing film 110 can be pierced by deploying slide 40/60 out of housing 20 for male connection, or peel sealing film 110 can be removed for female connection by pealing it off.

In an exemplary implementation, threads 45 or 65 can comprise female threads using a PosiFlush™ tip cap design for a male luer end, sufficient to interlock with a mating feature 86 of collar 84 of a male luer end, or connector, 80 to form a leak proof seal of cap 10 or 70 with connector 80. Such an exemplary implementation is applicable where connector 80 comprises a stopcock design to facilitate maintenance of pressure in an IV system when capped by cap 10 or 70.

In an exemplary implementation, one or more threads 25 can be sufficient to interlock with a mating feature 74 (such as one or more protrusions, lugs and/or thread) of a hub or tip 72 of needleless connector 70, as described for example in related U.S. patent application Ser. Nos. 15/408,278 and 15/408,187, both filed on Jan. 17, 2017.

According to yet further exemplary implementations of the embodiments of the disclosure, in cap 10 or 70 described above with reference to FIGS. 2 through 9C, at least a female lure capping portion, or cavity 27, can be implemented with various venting features and designs described in US patent applications Nos. U.S. patent application Ser. Nos. 15/408,278 and 15/408,187, both filed on Jan. 17, 2017, for example by modifying shape and/or size and/or configuration (such as pitch, spacing, thickness, and/or other structural features) of thread 25 and/or configuration of interior surface of interior sidewall 22.

While the present disclosure has been shown and described with reference to certain exemplary embodiments thereof, it will be understood by those skilled in the art that various changes in form and details may be made therein without departing from the spirit and scope of the embodiments of the present disclosure. For example, the inner and/or the outer housing of the cap, and/or the base, and/or the slide, and or the rod, can be single shot molded, or made by other suitable process. Furthermore, any of the features or elements of any exemplary implementations of the embodiments of the present disclosure as describes above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of disclosure.

Other objects, advantages and salient features of the disclosure will become apparent to those skilled in the art from the details provided, which, taken in conjunction with the annexed drawing figures, disclose exemplary embodiments of the disclosure.

I claim:

1. A cap comprising:
an housing comprising an open first end with a first opening to a first cavity within said housing for receiving a female connector, said open first end having an interior surface configured to engage said female connector;
a base axially fixed with respect to said housing and rotatable with respect to said housing;
a slide configured within said housing and comprising a second opening into a second cavity configured to receive an hub of a male connector, and an exterior surface configured to engage said male connector; and
an inner thread on said interior surface configured to engage said female connector,
wherein said slide interfaces with said base such that
a first rotation of said base in a first direction with respect to said housing causes said slide to project out of said housing through said first cavity and via said first opening to receive and engage said male connector, and
a second rotation of said base in a second direction opposite to said first direction with respect to said housing causes said slide to retract into said housing to allow access to said first cavity to receive and engage said female connector, and
when said hub of said female connector is received within said first cavity, said hub of said female connector is secured within said first cavity by interlocking at least a portion of said inner thread with a mating feature on said hub of said female connector.

2. The cap of claim 1 further comprising:
a rod configured to project out of or retract into said second cavity,
wherein said rod interfaces with said base such that after said second rotation said rod projects into said first cavity to interact with said received and engaged female connector.

3. The cap of claim 2, wherein:
said rod interfaces with said base such that a third rotation of said base further in said second direction causes said rod to retract into said housing and out of said first cavity avoiding interaction of said rod with said received and engaged female connector.

4. The cap of claim 3, wherein said housing comprises:
an essentially cylindrical interior sidewall defining said first opening at a top of said housing, and
an essentially cylindrical exterior sidewall defining a third opening at a bottom of said housing.

5. The cap of claim 3 further comprising:
an inner thread on said interior surface configured to engage said female connector,
wherein:
when said hub of said female connector is received within said first cavity, said hub of said female connector is secured within said first cavity by interlocking at least a portion of said inner thread with a mating feature on said hub of said female connector.

6. The cap of claim 3 further comprising:
an outer thread on said exterior surface configured to engage said male connector,
wherein:
when said hub of said male connector is received within said second cavity, said hub of said male connector is secured within said second cavity by interlocking at least a portion of said outer thread with a mating feature of said male connector.

7. The cap of claim 2, wherein said housing comprises:
an essentially cylindrical interior sidewall defining said first opening at a top of said housing, and
an essentially cylindrical exterior sidewall defining a third opening at a bottom of said housing.

8. The cap of claim 2 further comprising:
an outer thread on said exterior surface configured to engage said male connector,
wherein:
when said hub of said male connector is received within said second cavity, said hub of said male connector is secured within said second cavity by interlocking at least a portion of said outer thread with a mating feature of said male connector.

9. The cap of claim 2, wherein:
said housing and said base are engaged by a snap fit connection essentially fixing said housing and said base axially with respect to each other, and allowing essentially free rotation of said base and said housing with respect to each other.

10. The cap of claim 2, further comprising:
at least one removable cover sealing said first cavity.

11. The cap of claim 1, wherein said housing comprises:
an essentially cylindrical interior sidewall defining said first opening at a top of said housing, and
an essentially cylindrical exterior sidewall defining a third opening at a bottom of said housing.

12. The cap of claim 11 wherein
said base comprises:
  an essentially cylindrical sidewall,
  a bottom wall connected to said cylindrical sidewall, and
  a protrusion extending out of an interior surface of said bottom wall; and
said slide comprising:
  an essentially cylindrical structure comprising an upper portion and a lower portion, and said second cavity extending axially through said cylindrical structure,
  wherein said second cavity at said upper portion is configure to receive said hub of said male connector,
  exterior surface of said upper portion is configure to engage said male connector,
  interior surface of said lower portion is configured to interface with said protrusion of said base to allow said slide to translate axially and radially with respect to said base, and
  exterior surface of said lower portion is configured to interface with an interior of said essentially cylindrical exterior sidewall of said housing to allow said slide to translate axially with respect to said housing and to essentially fix said slide rotationally with respect to said housing.

13. The cap of claim 12, wherein:
said cylindrical exterior sidewall, said cylindrical interior sidewall, said first opening, said second opening, said third opening, said cylindrical sidewall, and said protrusion are co-axial.

14. The cap of claim 12 wherein:
said protrusion of said base comprises a thread; and
said interior surface of said lower portion of said slide comprises a groove corresponding to said thread.

15. The cap of claim 1 further comprising:
an outer thread on said exterior surface configured to engage said male connector,
wherein:
when said hub of said male connector is received within said second cavity, said hub of said male connector is secured within said second cavity by interlocking at least a portion of said outer thread with a mating feature of said male connector.

16. The cap of claim 15 wherein:
said mating feature of said male connector comprises a thread, and said outer thread comprises a full thread corresponding to said thread of said mating feature of said male connector.

17. The cap of claim 1, wherein:
said housing and said base are engaged by a snap fit connection essentially fixing said housing and said base axially with respect to each other, and allowing essentially free rotation of said base and said housing with respect to each other.

18. The cap of claim 1, further comprising:
at least one removable cover sealing said first cavity.

19. A cap comprising:
an housing comprising an open first end with a first opening to a first cavity within said housing for receiving a female connector, said open first end having an interior surface configured to engage said female connector;
a base axially fixed with respect to said housing and rotatable with respect to said housing;
a slide configured within said housing and comprising a second opening into a second cavity configured to receive an hub of a male connector, and an exterior surface configured to engage said male connector; and
an outer thread on said exterior surface configured to engage said male connector,
wherein said slide interfaces with said base such that
  a first rotation of said base in a first direction with respect to said housing causes said slide to project out of said housing through said first cavity and via said first opening to receive and engage said male connector, and
  a second rotation of said base in a second direction opposite to said first direction with respect to said housing causes said slide to retract into said housing to allow access to said first cavity to receive and engage said female connector, and
when said hub of said male connector is received within said second cavity, said hub of said male connector is secured within said second cavity by interlocking at least a portion of said outer thread with a mating feature of said male connector.

20. The cap of claim 19, wherein:
said mating feature of said male connector comprises a thread, and said outer thread comprises a full thread corresponding to said thread of said mating feature of said male connector.

21. A cap comprising:
an housing comprising an open first end with a first opening to a first cavity within said housing for receiving a female connector, said open first end having an interior surface configured to engage said female connector;
a base axially fixed with respect to said housing and rotatable with respect to said housing; and
a slide configured within said housing and comprising a second opening into a second cavity configured to receive an hub of a male connector, and an exterior surface configured to engage said male connector,
wherein said slide interfaces with said base such that
a first rotation of said base in a first direction with respect to said housing causes said slide to project out of said housing through said first cavity and via said first opening to receive and engage said male connector, and
a second rotation of said base in a second direction opposite to said first direction with respect to said housing causes said slide to retract into said housing to allow access to said first cavity to receive and engage said female connector;
said housing comprises:
an essentially cylindrical interior sidewall defining said first opening at a top of said housing, and
an essentially cylindrical exterior sidewall defining a third opening at a bottom of said housing;
said base comprises:
an essentially cylindrical sidewall,
a bottom wall connected to said cylindrical sidewall, and
a protrusion extending out of an interior surface of said bottom wall; and
said slide comprises:
an essentially cylindrical structure comprising an upper portion and a lower portion, and said second cavity extending axially through said cylindrical structure,
wherein said second cavity at said upper portion is configure to receive said hub of said male connector,
exterior surface of said upper portion is configure to engage said male connector,
interior surface of said lower portion is configured to interface with said protrusion of said base to allow said slide to translate axially and radially with respect to said base, and
exterior surface of said lower portion is configured to interface with an interior of said essentially cylindrical exterior sidewall of said housing to allow said slide to translate axially with respect to said housing and to essentially fix said slide rotationally with respect to said housing.

22. The cap of claim 21, wherein:
said cylindrical exterior sidewall, said cylindrical interior sidewall, said first opening, said second opening, said third opening, said cylindrical sidewall, and said protrusion are co-axial.

23. The cap of claim 21, wherein:
said protrusion of said base comprises a thread; and
said interior surface of said lower portion of said slide comprises a groove corresponding to said thread.

24. A cap comprising:
an housing comprising an open first end with a first opening to a first cavity within said housing for receiving a female connector, said open first end having an interior surface configured to engage said female connector;
a base axially fixed with respect to said housing and rotatable with respect to said housing;
a slide configured within said housing and comprising a second opening into a second cavity configured to receive an hub of a male connector, and an exterior surface configured to engage said male connector; and
a rod configured to project out of or retract into said second cavity,
wherein said slide interfaces with said base such that
a first rotation of said base in a first direction with respect to said housing causes said slide to project out of said housing through said first cavity and via said first opening to receive and engage said male connector, and
a second rotation of said base in a second direction opposite to said first direction with respect to said housing causes said slide to retract into said housing to allow access to said first cavity to receive and engage said female connector,
said rod interfaces with said base such that
after said second rotation said rod projects into said first cavity to interact with said received and engaged female connector, and
a third rotation of said base further in said second direction causes said rod to retract into said housing and out of said first cavity avoiding interaction of said rod with said received and engaged female connector.

25. The cap of claim 24, wherein said housing comprises:
an essentially cylindrical interior sidewall defining said first opening at a top of said housing, and
an essentially cylindrical exterior sidewall defining a third opening at a bottom of said housing.

26. The cap of claim 24 further comprising:
an inner thread on said interior surface configured to engage said female connector,
wherein:
when said hub of said female connector is received within said first cavity, said hub of said female connector is secured within said first cavity by interlocking at least a portion of said inner thread with a mating feature on said hub of said female connector.

27. The cap of claim 24 further comprising:
an outer thread on said exterior surface configured to engage said male connector,
wherein:
when said hub of said male connector is received within said second cavity, said hub of said male connector is secured within said second cavity by interlocking at least a portion of said outer thread with a mating feature of said male connector.

28. A cap comprising:
an housing comprising an open first end with a first opening to a first cavity within said housing for receiving a female connector, said open first end having an interior surface configured to engage said female connector;
a base axially fixed with respect to said housing and rotatable with respect to said housing;
a slide configured within said housing and comprising a second opening into a second cavity configured to receive an hub of a male connector, and an exterior surface configured to engage said male connector;
a rod configured to project out of or retract into said second cavity; and
an outer thread on said exterior surface configured to engage said male connector,
wherein said slide interfaces with said base such that
  a first rotation of said base in a first direction with respect to said housing causes said slide to project out of said housing through said first cavity and via said first opening to receive and engage said male connector, and
  a second rotation of said base in a second direction opposite to said first direction with respect to said housing causes said slide to retract into said housing to allow access to said first cavity to receive and engage said female connector,
said rod interfaces with said base such that
  after said second rotation said rod projects into said first cavity to interact with said received and engaged female connector, and
when said hub of said male connector is received within said second cavity, said hub of said male connector is secured within said second cavity by interlocking at least a portion of said outer thread with a mating feature of said male connector.

* * * * *